(12) United States Patent
May (10) Patent No.: US 7,418,294 B2
(45) Date of Patent: Aug. 26, 2008

(54) ELECTRO-THERAPEUTIC DEVICE (76) Inventor: Hans-Ulrich May, Albert Einstein Strasse 1, D-75015 Bretten (DE)

( * ) Notice: Subject to any disclaimer, the term of this patent is extended or adjusted under 35 U.S.C. 154(b) by 264 days.

(21) Appl. No.: 10/344,383

(22) PCT Filed: Aug. 10, 2001

(86) PCT No.: PCT/DE01/02983

§ 371 (c)(1),
(2), (4) Date: Feb. 11, 2003

(87) PCT Pub. No.: WO02/13904

PCT Pub. Date: Feb. 21, 2002

(65) Prior Publication Data

US 2003/0176901 A1 Sep. 18, 2003

(30) Foreign Application Priority Data

Aug. 11, 2000 (DE) .............................. 100 39 240

(51) Int. Cl.
*A61N 1/06* (2006.01)

(52) U.S. Cl. ............................... 607/42; 607/3; 607/76; 600/545

(58) Field of Classification Search ................... 607/76, 607/42, 3; 128/905; 600/545
See application file for complete search history.

(56) References Cited

U.S. PATENT DOCUMENTS

| 3,773,051 | A | * | 11/1973 | Holcomb et al. | 607/61 |
| 3,821,949 | A | * | 7/1974 | Hartzell et al. | 600/545 |
| 3,837,331 | A | * | 9/1974 | Ross | 600/27 |
| 3,875,930 | A | * | 4/1975 | Silva et al. | 600/545 |
| 4,071,033 | A | * | 1/1978 | Nawracaj et al. | 607/67 |
| 4,243,043 | A | | 1/1981 | Kazimirov et al. | |
| 4,922,908 | A | | 5/1990 | Morawetz et al. | |
| 5,123,413 | A | * | 6/1992 | Hasegawa et al. | 607/2 |
| 5,131,389 | A | * | 7/1992 | Giordani | 607/47 |
| 5,350,414 | A | | 9/1994 | Koken | |
| 5,573,552 | A | | 11/1996 | Hansjurgens | |
| 5,718,662 | A | | 2/1998 | Jalinous | |
| 5,891,185 | A | * | 4/1999 | Freed et al. | 607/72 |
| 6,161,044 | A | * | 12/2000 | Silverstone | 607/45 |
| 6,760,627 | B2 | * | 7/2004 | Carter et al. | 607/69 |

* cited by examiner

Primary Examiner—Carl H. Layno
Assistant Examiner—Deborah Malamud
(74) Attorney, Agent, or Firm—Collard & Roe, P.C.

(57) ABSTRACT

In the field of electrotherapy, there are currently known devices and methods, in which either the frequency or the amplitude of a therapeutic current is varied. According to a representation of the amplitude on a logarithmic frequency scale, said methods are designated correspondingly as methods of vertical or horizontal stimulation. Various advantages and disadvantages are associated with both methods. The invention relates to a device for carrying out an electrotherapeutic method, according to which the amplitude (A) and the frequency (f) of the therapeutic current ($i_B$) are simultaneously varied within a therapeutic frequency band ($f_B$), which lies in the medium frequency range, in such a way that the method is carried out in discrete frequency steps, either in the range of different frequencies lying just below a stimulation threshold (RS), or periodically between a stimulation that lies above the threshold and a stimulation that lies below said threshold.

15 Claims, 3 Drawing Sheets

ELECTRO-THERAPEUTIC DEVICE

CROSS REFERENCE TO RELATED APPLICATIONS

Applicant claims priority under 35 U.S.C. §119 of German Application No. 100 39 240.7, filed Aug. 11, 2000. Applicant also claims priority under 35 U.S.C. §365 of PCT/DE01/02983, filed Aug. 10, 2001. The international application under PCT article 21(2) was not published in English.

BACKGROUND OF THE INVENTION

The invention relates to an electro-therapeutic device for the treatment of the preferably human body with electrical currents having a defined frequency and amplitude. The device comprises at least two flat electrodes that can be connected with the body to be treated, for closing a current circuit via said body, in connection with which a treatment current, the amplitude (A) and frequency (f) of which can be simultaneously modulated, can be introduced into the body to be treated.

Such a device is known already from the Japanese patent application JP 5-212 126 A.

A similar device, which, however, is operated without simultaneous modulation of the amplitude and frequency, is known from the European patent specification EP 0 659 099 B1.

A distinction is made in connection with this known electro-therapeutic device between two methods of application of stimulation current:
the "polar stimulation principle" that is depending on the polarity; and
the "non-polar stimulation principle that is independent of the polarity.

The polarity stimulation principle is applicable to low-frequency currents in the range of from 0 to 200 Hz, and the non-polar stimulation principle is applicable to so-called medium-frequency currents in the range of from about 1 to 100 kHz.

Furthermore, in the field of electro-therapy, a distinction can be made between stimulation effects that depend on the frequency, and stimulation effects that are independent of the frequency. Furthermore, methods are known that elevate these effects in an isolated manner and combine them with each other in a useful manner.

In connection with the methods depending on the frequency, the frequency of the treatment current is varied, and the amplitude of the treatment current is varied in connection with the methods depending on the amplitude.

If, in a double-logarithmic system of coordinates, the thresholds of the frequency are represented as a function of the frequency, whereby the intensity of the voltage or current are represented as ordinate values and the frequencies as abscissa values, the result is an approximately straight-line development of the curve. However, the developing curve is ascending in an approximately straight-lined manner only because the intensity threshold values rise to a relatively higher degree as the frequency values are rising, so that the ascent of the curve grows to a minor extent with the increase in the frequency accordingly. Expressed in other words, the approximately straight-lined curve "is sagging through a little".

The aforementioned, only approximately straight-lined development of the curve represents the stimulation threshold, thus -a frequency-dependent intensity threshold value that is triggering action potentials when it is exceeded.

The frequency at which this threshold is repeatedly exceeded due to repeated variation of the amplitude, determines the frequency at which the above-mentioned action potentials are triggered in conjunction with the stimulation method depending on the amplitude.

In the aforementioned system of coordinates, the treatment currents applied in the field of electro-therapy depending on the frequency are flowing in a horizontal straight line, and the treatment current generated in the case of the treatment depending on the amplitude are flowing on a vertical straight line.

The two methods are accordingly referred to also the horizontal and the vertical stimulation.

Purely below-threshold applications are known in connection with both methods are well if, in the therapy, importance is attributed to effects other than the described stimulation effects.

The successes achieved in electro-therapy primarily relate to the areas of alleviating pain, the stimulation of cross-striated and smooth musculature, of influencing the blood circulation and the metabolism; inhibition of inflammation, and promotion of the regeneration in the area of healing wounds and bones.

The basis for the therapeutic spectrum of currents are their physical parameters and the influences that are derived from these parameters and are acting on the functions of the structures of the biological systems being treated.

Such parameters of the current are most of all the frequency with its modulations; the modulation frequencies; and the intensity parameters such as the voltage, the current intensity, the output; the locally effective field strength; the current density, the output density etc., as well as in turn their modulation as the amplitude modulation at the amplitude modulation frequency and the degree of modulation.

In connection with currents, a distinction has to be made between systemic and local compatibility, as it has to be made in connection with pharmaceuticals.

The systemic compatibility of currents is determined most of all by the electro-toxic dosage required for triggering cardiac ventricular fibrillation, or for triggering epileptic attacks.

The "poorest" local compatibility is exhibited by direct current because of the risk of causing local burns and cauterization. Low-frequency currents are quite incompatible as well because of the poor manner in which they can be introduced into the body transcutaneously, and the low local pain thresholds deriving therefrom. Furthermore, in most cases, low-frequency currents also comprise a direct-current component with the problems mentioned above.

The disadvantages of low-frequency currents and of direct current can be avoided in connection with the so-called "horizontal stimulation" in the intermediate frequency range between 1 kHz and 100 kHz according to the device known already from EP 0 659 099 B1. The principle consists in that in the system of coordinates mentioned above, a horizontal low-frequency change in the carrier frequency takes place in such a manner that a variation is effected between an above-threshold and a below-threshold carrier frequency range, i.e. the medium-frequency carrier frequencies are frequency-modulated at a low frequency.

In this connection, the method of horizontal stimulation is not free of drawbacks either. In order to reach the threshold of a group of sensitive motor or sympathetic nerve fibers, the intensities are raised to the same extent between an upper and a lower corner frequency. The threshold of a nerve fiber is first exceeded in this connection with the lower corner frequency. After the threshold has been reached, the duration of the above-threshold state in the range of the lower carrier frequencies is still short as compared to the below-threshold state in the range of the higher carrier frequencies.

If the number of nerve fibers stimulated above the threshold is to be increased in order to raise, for example the intensity of the muscular contraction via a greater number of stimulated motor nerve fibers, or via a greater number of sensitive sympathetic fibers, or for the purpose of amplifying the intensity of the counter-irritation for the alleviation of pain, or for the purpose of intensifying peripheral effects of vasoconstriction via a greater number of sympathetic fibers, the duration of the above-threshold state is prolonged for the fibers whose threshold have been exceeded first, and the duration of the below-intensity state is reduced, and if the intensity is raised further, even the entire modulation period may be in the above-threshold range.

A continually growing number of nerve fibers are in fact stimulated above the threshold with each increase in the intensity; however, the "above-the-threshold" time increases at the same time for the fibers already stimulated above the threshold, so that due to the omission of interruption via the generation of volatile excitomotor activity, a permanent polarization with corresponding blocking may finally entail.

For a major part of the fibers, the modulation of the frequency therefore still takes place only in the above-threshold range.

In that case, the desired range of stimulation that is synchronous with the stimulation frequency is vacated and the range of the volatile excitomotor activity is entered into instead, without any clear relation to the stimulation frequency and discharge frequency of the stimulated structure in terms of time. Finally, the risk is posed that a permanent polarization of the cells is caused, i.e. of the nerves or muscles that actually should have been stimulated. In connection with nerves, the local permanent polarization leads to line blockage, and in connection with muscles to a reversible physiological contraction.

For these reasons, it is not possible according to the method of horizontal stimulation to generate maximal tetanic contractions, as it is possible by means of vertical stimulation.

According to EP 0 659 099, a further field of application of horizontal stimulation consists in the generation of so-called interferences. In this connection, two medium-frequency currents that have only minor frequency deviations among each other, are superimposed for generating low-frequency interference currents. An amplitude modulation ensues in the field of superimposition of the medium-frequency currents mentioned above. The modulation of the amplitude is caused by the difference in the frequency of the two medium-frequency currents supplied. The aim of such a superimposition of two or more current circuits is to raise the intensity of the treatment by adding up the individual intensities, so that action potentials or heat are generated in this range.

In this connection, a distinction can be made between phases of the pure heat treatment, and of the heat treatment with action potentials and treatment pauses, by controlling the method accordingly.

During the treatment pauses, in which neither heat nor action potentials are generated, a non-stimulatory metabolism effect remains that is referred to as the so-called "green metabolic effect". This designation is to be understood as being the delimitation vis-à-vis the "yellow stimulation effect", in connection with which the groups of nerves are stimulated in a targeted and stimulating manner.

In the interference therapy, the current circuits are applied by means of the respective electrodes in such a manner that the field of superimposition develops in the respective region of treatment.

A further drawback of the device already known from EP 0 659 099 consists in that relative long pauses of the sensitive perception are unavoidable in connection with the so-called slow horizontal frequency modulation. Only "green metabolic effects" are expected during these pauses; however, these effects could be exploited in a more efficient manner with an amplitude that is higher than the one usually applied in connection with this method.

In addition to the prior art described in the foregoing, devices have become available in the market in the meantime in conjunction with which it is possible to select between methods of the vertical and methods of the horizontal stimulation. This younger generation of devices is therefore adapted to carrying out both methods alternatively.

The invention is based on the problem of providing an electro-therapeutic device that avoids the drawbacks of the prior art and offers a constant level of the safety standard in conjunction with increased treatment comfort and an expanded field of application.

The object constituting the basis of the invention is resolved by an electro-therapeutic device according to the features of the invention. Advantageous further developments of the invention are also specified.

Owing to the fact that according to the invention, a treatment current is generated that is simultaneously amplitude- and frequency-modulated within a medium-frequency range of from 1 to 100 kHz, and that this current is introduced into the body to be treated, the benefits and possibilities of horizontal and vertical stimulation are united in one single method, on the one hand, and, furthermore, the shortcomings that are necessarily inherent to these methods are avoided on the other.

SUMMARY OF THE INVENTION

The electro-therapy that can be carried out with the device as defined by the invention is referred to as the high-tone frequency therapy that is based on the selected frequency range. This frequency range corresponds for the most part with the frequency range that can be perceived by the healthy, youthful human ear as high-tone sound. The selection of this frequency range ensures that the reduced capability of introducing current at lower frequencies is avoided, and that the required "distance" from the threshold of cardiac ventricular fibrillation is maintained. Because of the higher thresholds connected with the legally permissible intensities, higher frequencies would only generate weaker or even no neurophysiological stimulation effects, and could raise the risk of damage to the skin caused by heat due to lack of perception of the current.

The device as defined by the invention is intended for primarily treating the following:
  Painful diseases of the joints such as arthroses;
  pain in the back and the neck with related diseases of the spine;
  muscle distortions;
  pain and swelling after injuries and surgical interventions, including fading of the effects of local anesthetics, among others;
  normal, retarded and permanent healing processes, for example effusions of blood, bone fractures, ulcers of the lower leg, and pressure sores;
  venereal diseases and edemas.

Furthermore, local anesthesia can be produced in connection with the device as defined by the invention.

The electro-therapeutic device as defined by the invention additionally has an effect facilitating the metabolism on account of its shaking effect, because the promotion of diffusion processes leads to an enhanced supply to and effusion from living tissue, to an increase in the probability of contact between enzymes and the substrate; to an increase in the probability of generating resonance phenomena, as well as to the generation of effects imitating hormones via the influence exerted on the formation of cAMP in the cells.

By using non-modulated high-tone frequency currents, the device can be applied for generating local nerve blockage, for example in pain therapy or for local anesthesia. Furthermore, with the device as defined by the invention it is possible to introduce substantially higher current capacities while taking into account the local compatibility.

In this connection, the simultaneous modulation of the amplitude and frequency of the treatment current is carried out in a manner such that the method is varied between a first limit value with the low frequency $f_o$ and an upper or lower amplitude $A_o$ or $A_u$, respectively, of the treatment current $i_b$, and a second limit value with a high frequency $f_o$ and a lower or upper amplitude $A_u$ or $A_o$, respectively whereby an angle that can be preset is intersected in relation to the individual threshold of the treated patient that is either substantially parallel with said threshold, or the latter is crossed at said angle.

Within the medium-frequency range, a frequency band advantageously comprising up to three octaves is specified for carrying out the treatment. This frequency band is ranging from 4,096 to 32,768 Hz and thus predominantly in the audible range, and therefore between an audible, very high C, and the first C that is no longer safely audible. In order to generate therapeutically usable resonance phenomena, the frequency band should amount to at least one octave.

In an advantageously further developed embodiment, the electro-therapeutic device permits a treatment method in conjunction with which the treatment with current is carried out within the frequency band with constant modulation of the frequency and amplitude slightly below or above the threshold.

The treatment current is supplied in this connection via a control/regulation of the voltage or the current in a manner such that the treatment current is trailing the threshold slightly below or above the threshold.

For this purpose, the parameters for the device can be advantageously fixed in such a manner that a first limit value is adjusted first to a lower frequency in such a manner that the amplitude of the current is raised with no change in the frequency until this is slightly perceived by the patient. This value is stored in the operating memory of the electro-therapeutic device as the lower limit value. Subsequently, an upper limit value is adjusted to a predefined upper frequency by raising the current or voltage amplitude at the constant upper frequency until the current is slightly perceived again by the patient. This value is stored as the upper limit value. The moderately ascending curve obtained with a double logarithmic representation of the current or the voltage is the curve of the treatment current. The frequency-dependent treatment current is now supplied adjusted to said curve with respect to frequency and modulation over the duration of the treatment time, which can be preset.

The therapy is then carried out by running through the frequency band. The preset frequency steps are applied in discrete frequency steps over a defined span of time. It is entirely possible that the time periods during which the individual, adjusted frequency steps are acting, are varying.

As already mentioned above, as an alternative, it is possible also to treat excitable cell by "flooding" such cells with current by means of the electro-therapeutic device in a manner alternating between above-threshold and below-threshold current. In this connection, the angle of intersection of the straight line representing the treatment current in the double logarithmic representation, can be adjusted with the stimulation threshold, preferably depending on the desired or required stimulation. A rough intersection angle, thus in about a range of between 45 and 90 degrees, stands for a "hard stimulation"; and a small angle of intersection, thus in about the range of between 0 and 45 degrees, stands for a "soft stimulation". A hard stimulation is deemed desirable, for example for superimposing pain by generation of a counter-stimulation, and a soft stimulation is desired if individual groups of muscles are to be impacted in a targeted manner.

In this connection, again the parameters can be fixed for the electro-therapeutic device also in the present case in a manner such that in the range of a preset lower limit frequency, a first limit value with a voltage amplitude corresponding with an above-threshold effect is picked up and stored, and a second limit value is stored thereafter at a frequency designated as the upper limit frequency, with a voltage amplitude corresponding with a below-threshold effect as the upper limit value.

As mentioned already before, the amplitude of the treatment voltage above the logarithmically plotted frequency of the treatment current represents a straight line intersecting the stimulation threshold.

In the present case, too, the defined frequency band intended for application in the treatment is run through in defined frequency steps, whereby it is entirely possible to allocate different treatment time periods to the frequency selected in the given case.

For carrying out the method descrbed above, the electro-therapeutic device comprises at least one current generator for generating the treatment current; an oscillator; and a frequency-setting device for modulating the frequency; as well as a corresponding element for setting the amplitude of the treatment current. In addition, provision is made for a processor unit with a corresponding memory unit for automatically carrying out the aforementioned steps of the treatment, as well as for storing the required limit values. The treatment currents modulated within the meaning of the invention are supplied via at least two flat electrodes that are connected to the electro-therapeutic device.

In addition, the electro-therapeutic device can be provided with a time controller as well as an automatic shutoff device.

In an advantageously further developed embodiment, the electro-therapeutic device is provided with a number of or at least two current circuits that are independent of one another and can be controlled or regulated, In this way, several patients can be treated at the same time, on the one hand, and can be treated independently of one another by different methods on the other.

Furthermore, the interference methods already mentioned above can be carried out with such devices.

In connection with a particularly advantageous embodiment, the electro-therapeutic device is provided with four independent current circuits for generating four different treatment currents.

The difference between the individual currents in terms of frequency should be extremely minor and be in a range of between 1/60 and 1/5 Hz. As distinguished from conventional interference current devices for generating low-frequency amplitude modulations, the minor frequency difference supplies an extremely slow periodicity. The cause for this is a correspondingly slow change in the direction of the development of the field lines generated in the body to be treated in each case by means of the applied current circuits. The periodicity of the change in the field lines approximately corresponds with the one of the vasomotion. This so-called slow stereo-interference permits the periodic inclusion of regions of the body that have to be treated in distinguishable ways.

For generating such minor frequency differences of the different currents to be supplied is connected with substantial expenditure in terms of control technology. Such expenditure can be avoided by working with a method of gradual phase shifting between the three currents instead of operating in the way of the so-called high-tone frequency treatment.

According to a yet further development of the invention, the frequencies applied in the way of the high-tone frequency treatment can be reproduced in the high-fidelity mode as well.

The electro-therapeutic device is connected for said purpose to a suitable device for reproducing the applied frequencies in such a manner.

In addition or as an alternative, even selected works of music can be used for generating the treatment currents.

For said purpose, the electro-therapeutic device is equipped with a high-pass filter for filtering out the critical low frequencies, and the amplifier for generating the treatment current is provided with a corresponding output limitation in order to limit any critical output values that may occur in the way of the dynamics of the works of music used.

The music therapy described above, which adds to the stimulation perceived by the body a sensual high-fidelity impression, can be intensified by the application of visualization.

The electro-therapeutic device is actively connected for that purpose with a control device for controlling a lighting system with changing colors for visualizing the supplied frequencies in color.

BRIEF DESCRIPTION OF THE DRAWINGS

The invention is explained in greater detail in the following with the help of the drawings, in which.

DETAILED DESCRIPTION OF THE INVENTION

Figure 1:
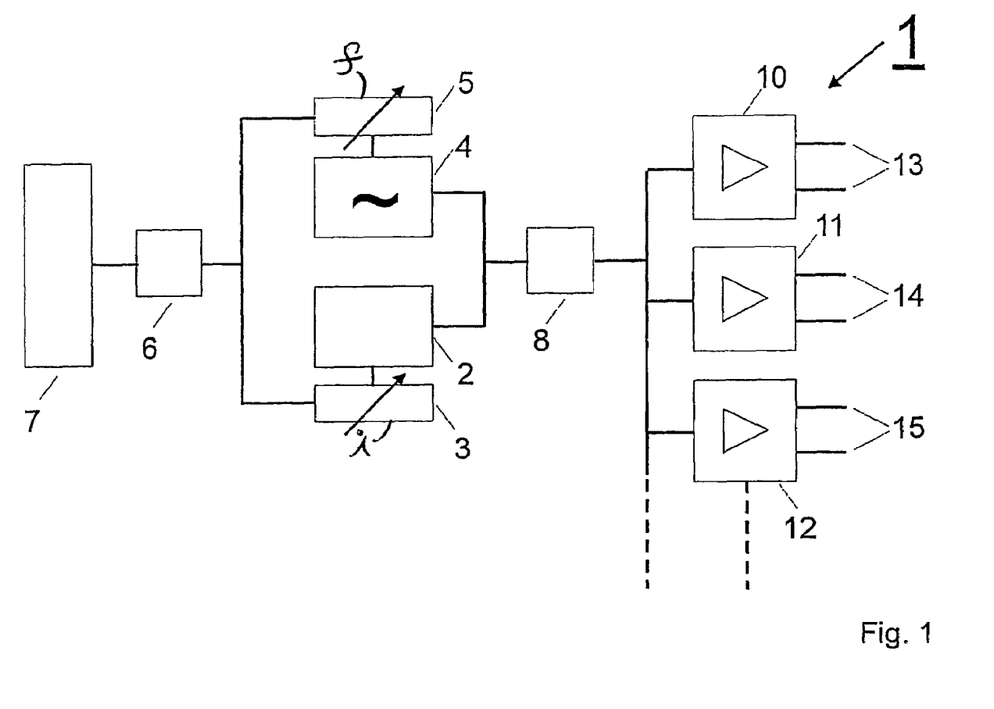
FIG. 1 is a block diagram of the electro-therapeutic device.

FIG. 1 shows an electro-therapeutic device in the form of a block circuit device 1. The device 1 is comprised of a current generator 2, whereby the amplitude of the current can be adjusted via a setting element 3. Furthermore, provision is made for an oscillator 4 that is connected to a frequency-setting device 5. The setting element 3 and the frequency-setting device 5 are controlled at least indirectly via the outputs of a microprocessor 6 that is data-connected with an operating memory 7. Via the current generator 2 and the frequency-setting device 5, a treatment current $I_B$, the amplitude A or the intensity of which are adjusted via the setting element 3, and its frequency f is adjusted via the frequency-setting device 5, is supplied depending on a treatment program. This program is controlled by the microprocessor 6 in conjunction with the values stored in the operating memory 7, or as a result of fixed parameters stored in the operating memory 7. The treatment current $I_b$ generated in said manner can be used for feeding it into three or more different current circuits that are generated by means of a superpositioning device 8.

Each current circuit comprises for this purpose its own amplifier unit 10 to 12 with its own frequency generation by means of suitable setting elements. The frequencies can be generated completely independently of each other with a defined relation to each other.

The flat electrodes 13 to 15 can be connected to the amplifier outputs for connecting them with the body to be treated.

Instead of being provided with the three current circuits shown in FIG. 1, it is possible also to equip the electro-therapeutic device with only one single or also even more independent current circuits.

Figure 4:
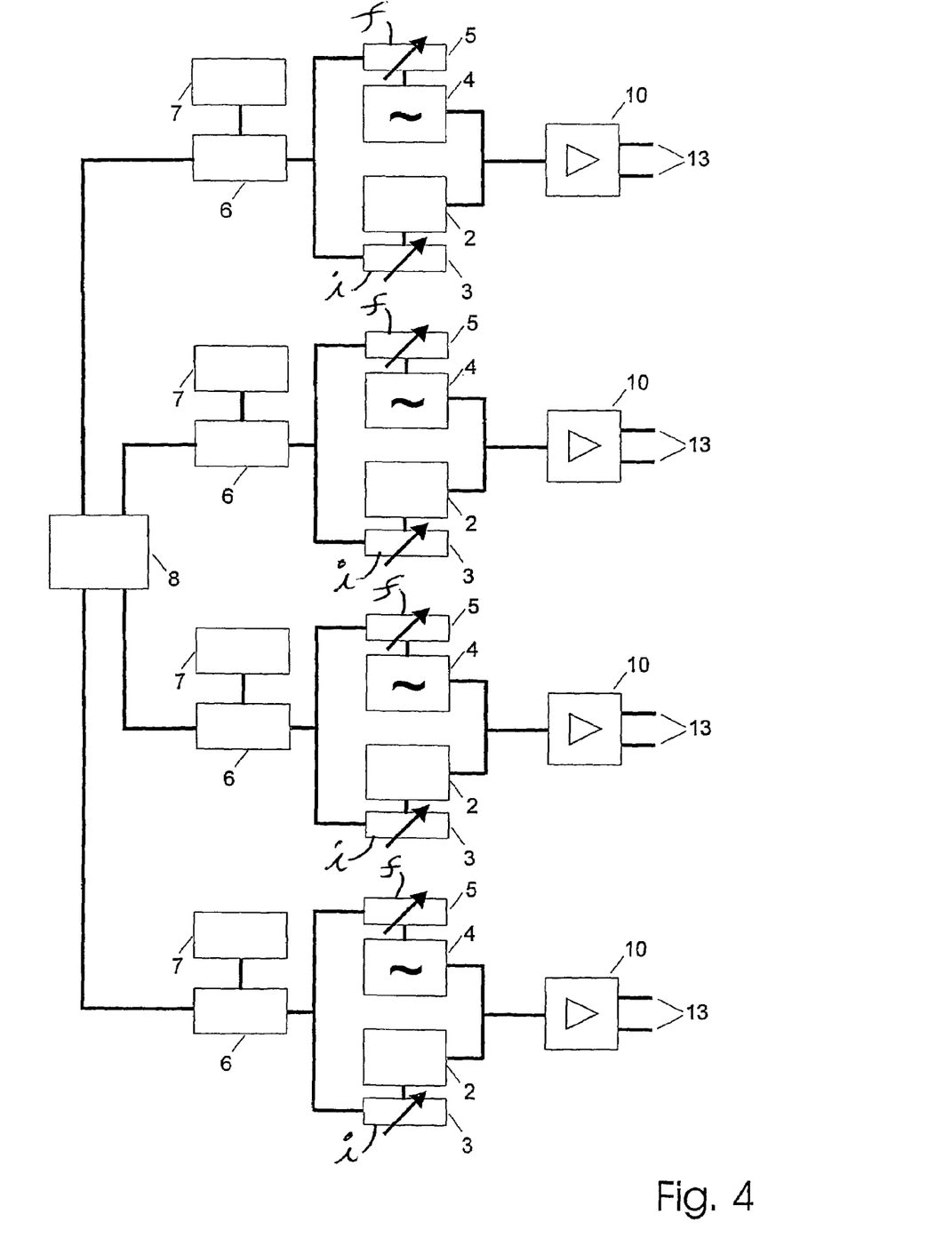
FIG. 4 shows the block diagram of another embodiment of the electro-therapeutic device.

In this connection, the independent current circuits also may be realized in a completely self-sufficient manner, thus not by means of any superposition. The technical design of such a variation is shown in FIG. 4.

Two preferred treatment methods of the electro-therapeutic therapy to be carried out with the electro-therapeutic device 1 are described in the following.

Figure 2:
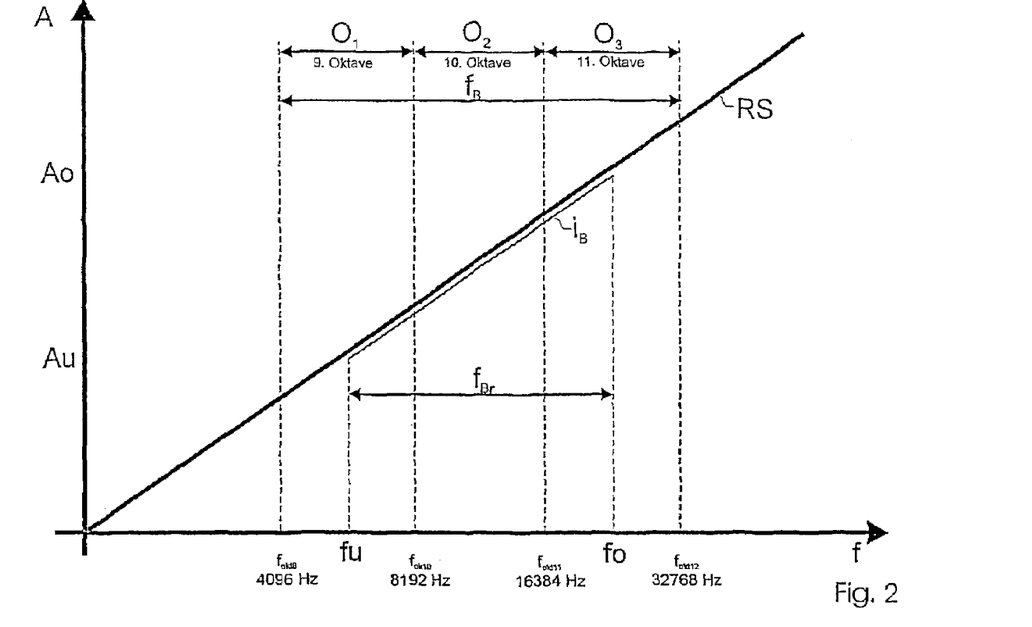
FIG. 2 is a diagram for the treatment below the threshold.

FIG. 2 shows a method of the sensitive below-threshold therapy. The current amplitude A above the frequency f is plotted on the logarithmic scale as shown in the diagram in FIG. 2. The treatment takes place within a medium-frequency range of 4,096 Hz to 32,768 Hz. This range is designated as the treatment frequency band $f_B$. The frequency band $f_B$ comprises the three octaves $O_1$ to $O_3$, within which the treatment frequency can be varied. The patient-dependent, individual stimulation threshold RS can be plotted as a straight line within this current amplitude/frequency coordinate system in a logarithmic representation.

The stimulation threshold RS denotes the frequency- and amplitude-dependent limit value of the cells that can be stimulated. Above this limit value, at least one action potential is generated automatically. Within the maximally possible frequency band $f_B$, an upper and a lower frequency value $f_o$ and $f_u$, respectively, can be selected depending on the patient and the treatment therapy. The amplitude and the frequency of the treatment current $I_B$ are modulated within said upper and lower frequency values.

In that connection, the parameters are first laid down in such a manner that with a fixed lower limit frequency $f_u$, the voltage or current amplitude A is raised until a first perception of the patient takes place in the region that has to be treated. Thereafter, the amplitude is slightly reduced again, so that the sensation disappears again. This current amplitude value $A_o$ thus lies barely below the stimulation threshold RS. As soon as this value has been adjusted, it is stored as the lower limit value. Subsequently, with an upper frequency $f_o$ set, the voltage or current amplitude A is raised again until the patient feels a slight sensation again. The amplitude is then subsequently slightly reduced again, so that this sensation will disappear again. This current amplitude value $A_o$ is then stored as well as the upper limit value.

The frequency band disposed between the upper and the lower limit frequencies represents the frequency band $F_{Br}$ that is simultaneously relevant to the treatment to be carried out. Now, within this frequency band $F_{Br}$, the treatment current $i_B$ is then modulated in discrete frequency steps in such a manner that the current is shifted from a low limit value in the range of the lower limit frequency $f_u$ with a low amplitude $A_u$, into the range of higher frequencies until the upper limit frequency $f_o$ has been reached. In that connection, the current amplitude A is increased with the increasing frequency as well until a value $A_o$ has been reached. The current is increased or reduced in this connection parallel with the perception threshold within the relevant frequency band $F_{Br}$. It is entirely possible in this connection to select different values for the duration of the time span over which the voltage or current amplitudes A allocated to the individual frequencies are acting.

The metabolism of the body is favorably influenced or promoted in the course of this therapy in different planes of action, and a stimulating effect is consciously omitted.

Figure 3:
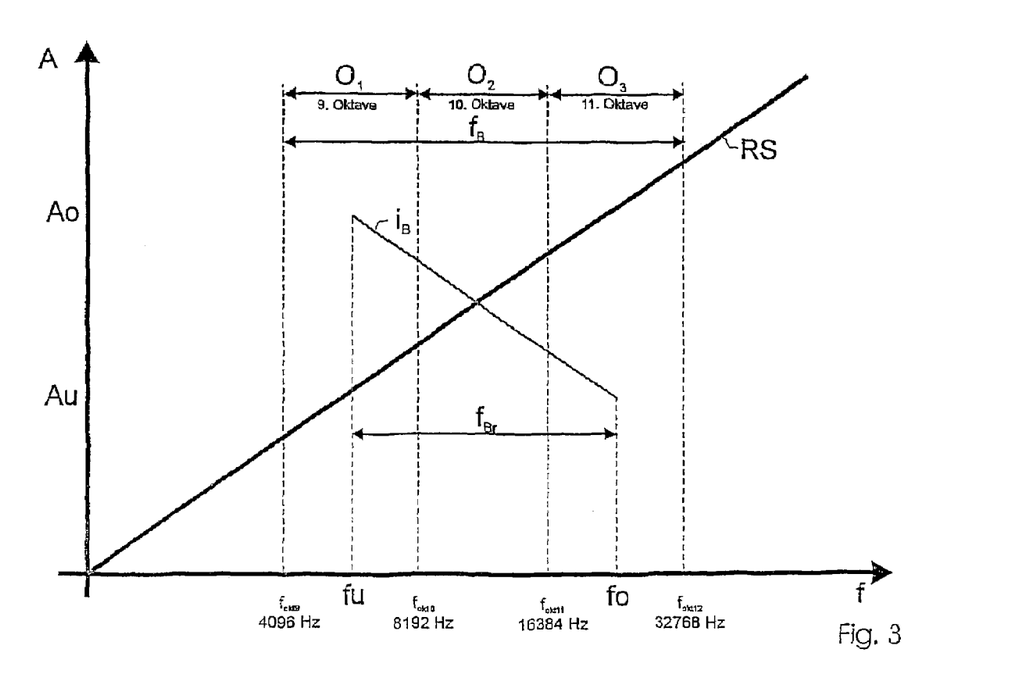
FIG. 3 is a diagram for the treatment above and below the threshold.

In connection with the methods represented in the diagram according to FIG. 3, the aim is to apply a stimulating effect in addition to the promotion of the metabolism.

The parameters of the treatment current $I_B$ are fixed in this connection in such a manner that a voltage or current amplitude $A_o$ of the treatment current $i_B$ is first selected in the range of the lower limit frequency $f_u$ in a manner such that a maximum amplitude $A_u$ is adjusted distinctly above the stimulation threshold. Subsequently, in the course of laying down the parameters, an upper limit frequency $f_o$ is picked up, whereby the amplitude value $A_u$ of the treatment current $I_B$ allocated to the upper limit frequency $f_o$ is obtained in the relation to the current amplitude $A_o$ allocated to the lower frequency. For example, the lower amplitude $A_u$ may amount to 50 percent of the upper amplitude $A_o$ of the treatment current $i_B$. In any case, the lower amplitude $A_u$ allocated to the upper limit frequency $f_o$ lies distinctly below the stimulation threshold RS. The treatment current $i_s$ modulated in the course of the treatment within the relevant frequency band $f_{BR}$ in such a manner that phases of the above and the below-threshold configurations replace each other periodically with corresponding frequency and amplitude-modulation-frequency-synchronous triggering of action potentials. In this connection as well, the relevant frequency band $f_{Br}$ is run through in discrete steps, whereby it is entirely possible to select in different ways the time duration over which the current amplitudes allocated to the individual frequencies are acting.

Furthermore, the alternating runs through the relevant frequency band $f_{BR}$ may occur rapidly at different rates of speed. In the present example, the relevant frequency band comprises two octaves.

With both methods, which are selected here only by way of example, the adjusted frequency range lies at least predominantly in the audible range. Therefore, it may be useful within the meaning of an overall uniform treatment to additionally provide the electro-therapeutic device 1 with equipment for reproducing the audible frequencies and the make the latter accessible to the patient. Alternatively, even the reversed approach is conceivable, which is to use selected works of music for controlling the electro-therapeutic device in a manner such that the treatment currents $i_B$ are selected depending on the harmonic configuration of the selected works of music. In that case, a high-pass filter for separating or weakening the intensity of the locally and systemically less compatible low frequencies has to be allocated to the electro-therapeutic device, and to the amplifier units 10 to 12 an output limitation in order to prevent the compatibility of the body to be exceeded in the way of the dynamics of individual works of music by introducing excessive outputs.

As a further development of the aforementioned overall idea of the therapy, it is possible to additionally allocate to the electro-therapeutic device a system for visualizing the frequencies employed, for example in the way of correspondingly controlled colored light games.

An electro-therapeutic device is thus described in the foregoing that combines within itself the advantages of the horizontal and the vertical stimulation and, in the presence of a raised safety standard, offers the highest operating comfort in conjunction with new application possibilities for the patient.

LIST OF REFERENCE SYMBOLS

1 Electro-therapeutic device
2 Current generator
3 Setting element
4 Oscillator
5 Frequency-setting device
6 Microprocessor
7 Operating memory
8 Superpositioning device
10 to 12 Amplifiers
13 to 15 Flat electrodes
$i_B$ Treatment current
A Amplitude
$A_o$ Upper amplitude
$A_u$ Lower amplitude
f Frequency
$f_B$ Frequency band
$f_{Br}$ Relevant frequency band
$O_1$ to $O_3$ Octaves
RS Stimulation threshold
$f_o$ Upper limit frequency
$f_u$ Lower limit frequency

The invention claimed is:

1. An electro-therapeutic device for treating the preferably human body, and/or for carrying out a respirator-triggered, active expiration and/or for the prophylaxis of an inactivity atrophy of the respiratory muscle disorder, with electrical currents of a defined frequency and amplitude, comprising
   at least two flat electrodes attachable to the body to be treated for closing a current circuit via said body, in connection with which device a treatment current ($i_B$) whose amplitude (A) and frequency (f) can be modulated simultaneously, can be introduced into the body to be treated,
   means for varying the treatment current ($i_B$) within a frequency band ($f_B$) designated as the medium frequency range between from 1 kHz to 100 kHz, in order to treat the preferably human body, or to carry out said active expiration or to treat said respiratory disorder, in a manner such that it is varied in preferably discrete frequency steps between a first limit value with a low limit frequency ($f_u$) at a simultaneously minimal amplitude ($A_u$) of the treatment current ($i_B$), and a second limit value with an upper limit frequency ($f_o$) with a maximal amplitude ($A_o$) of the treatment current ($i_B$) and a second limit value with an upper limit frequency ($f_o$) with a minimal amplitude ($A_u$) of the treatment current ($i_B$),
   means for causing amplitude rises or drops as the frequency is simultaneously increasing, or, viceversa, the amplitude (A) of the treatment current ($i_B$) decreases or rises as the frequency is simultaneously decreasing, and
   means for modulating the treatment current ($i_B$) in such a manner that it is varied at least within a part of the treatment frequency band ($f_B$) between the first and the second limit values in a manner such that it is varied slightly below the threshold based on a stimulation threshold (RS), substantially in parallel with the stimulation threshold (RS), in a manner such that the treatment current ($i_b$) is always trailing the stimulation threshold (RS) depending upon the amplitude and the frequency, in each case slightly falling short of the sensitivity threshold.

2. The electrotherapeutic device according to claim 1, comprising
   means for fixing the parameters of the electro-therapeutic device (1) in a manner such that at a lower frequency ($f_u$), the amplitude (A) of the treatment current ($i_b$) is raised up to barely below the stimulation threshold (RS) up to an amplitude value ($A_u$), and said amplitude value can be stored as the first limit value within an operating memory (7) of the electro-therapeutic device; and that at an upper limit frequency ($f_o$) that can be preset, the amplitude (A) of the treatment current ($i_B$) is again raised up to barely below the stimulation threshold (RS) up to an amplitude value ($A_o$) of the treatment current ($i_B$) and can be stored within the operating memory (7) as the second limit value.

3. The electro-therapeutic device according to claim 1, in connection with which device, the trailing takes place between the first and the second limit values in defined frequency steps, with a current amplitude (A) lying barely above or below the stimulation threshold (RS) being allocated to each of such steps.

4. The electro-therapeutic device according to claim 1, comprising means for modulating the treatment current ($i_B$) in such a manner that at least within a part of the frequency band ($f_B$), between the first limit value with a lower frequency ($f_u$), to which an amplitude ($A_o$) of the treatment current lying above the stimulation threshold (RS) is allocated, and a second limit value with an upper limit frequency ($f_o$), to which an amplitude ($A_u$) of the treatment current ($i_B$) lying distinctly below the stimulation threshold (RS) is allocated, the treatment current is varied in a manner such that the stimulation threshold (RS) is intersected in each case at an angle that can be preset in a variable manner.

5. The electro-therapeutic device according to claim 4, comprising means for fixing the parameters of the electro-therapeutic device in such a manner that at a lower frequency ($f_u$) that can be preset, an amplitude ($A_o$) of the treatment current ($i_B$) distinctly above the stimulation threshold (RS) is picked up and can be stored within the operating memory (7) as the first limit value, and following an upper limit frequency ($f_o$), an amplitude ($A_u$) of the treatment current($i_B$) lying distinctly below the stimulation threshold (RS) is determined in the form of a defined proportion of the amplitude ($A_o$) and filed within the operating memory (7) as the second limit value.

6. The electro-therapeutic device according to claim 4, wherein the method is carried out between the first and the second limit values in preferably discrete frequency steps in a manner such that the phases of the above-threshold and the below-threshold stimulation alternate periodically.

7. The electra-therapeutic device according to claim 4, comprising means for causing a relevant treatment frequency range ($f_{Br}$) lying between the lower limit frequency ($f_u$) and the upper limit frequency ($f_o$) to be run through at preferably different speeds that can be preset.

8. The electrotherapeutic device according to claim 7, wherein the device comprises a plurality, at least two current circuits operating independently of one another.

9. The electro-therapeutic device according to claim 8 comprising at least three, independent current circuits for generating interferences within the body to be treated, in a manner such that three treatment currents ($i_{B1}$ to $i_{B3}$) with a preferably variable, minor frequency difference preferably in the range of $1/60$ and $1/5$ Hz, can be simultaneously introduced into the body to be treated.

10. The electro-therapeutic device according to claim 8, wherein a gradual phase shift can be adjusted between the voltages or currents ($i_{B1}$ to $i_{B3}$) introduced by means of the different current circuits.

11. The electro-therapeutic device according to claim 8, wherein the frequencies (f) applied for treating the body are simultaneously reproducible audiophonically, and/or that defined works of music can be used for the therapeutic treatment or the modulation of the treatment current ($i_B$).

12. The electratherapeutic device according to claim 8, wherein a device for reproducing color and/or light is allocated to the electro-therapeutic device in such a manner that the frequencies applied for modulating the treatment current ($i_B$) can be simultaneously applied for controlling the light system in terms of a light and/or color visualization.

13. The electratherapeutic device according to claim 4, comprising a current or voltage generator (2) for generating the treatment current ($i_B$), the frequency of which generator can be modulated by means of an oscillator (4) and a frequency-setting device (5) allocated to said oscillator; and the amplitude of which can be modulated by a setting device (3); and with a processor unit (6) as well as a memory unit (7) allocated to said processor unit for controlling and/or regulating the electro-therapy, as well as comprising at least two flat electrodes (13 to 15) for attachment to a body to be treated in a contacting manner.

14. A method for using an electra-therapeutic device (1)

for carrying out a respirator-triggered, active expiration and/or for the prophylaxis of an inactivity atrophy of the respiratory muscle wherein said electro-therapeutic device for treating the preferably human body with electrical currents of a defined frequency and amplitude, comprising attaching at least two flat electrodes to the body to be treated for closing a current circuit via said body, in connection with which device a treatment current ($i_B$) whose amplitude (A) and frequency (f) can be modulated simultaneously, can be introduced into the body to be treated, varying the treatment current ($i_B$) within a frequency band ($f_B$) designated as the medium frequency range between from 1to 100kHz, in a manner such that it is varied in preferably discrete frequency steps between a first limit value with a low limit frequency ($f_u$) at a simultaneously minimal amplitude ($A_u$) of the treatment current ($i_B$), and a second limit value with an upper limit frequency ($f_o$) with a maximal amplitude ($A_o$) of the treatment current ($i_B$) and a second limit value with an upper limit frequency ($f_o$) with a minimal amplitude ($A_u$) of the treatment current ($i_B$), whereby the amplitude rises or drops as the frequency is simultaneously increasing, or, viceversa, the amplitude (A) of the treatment current ($i_B$) decreases or rises as the frequency is simultaneously decreasing; and wherein the treatment current ($i_B$) is modulated in such a manner that it is varied at least within a part of the treatment frequency band ($f_B$) between the first and the second limit values in a manner such that it is varied slightly below the threshold based on a stimulation threshold (RS), substantially in parallel with the stimulation threshold (RS), in a manner such that the treatment current ($i_B$) is always trailing the stimulation threshold (RS) depending upon the amplitude and the frequency, in each case slightly falling short of the sensitivity threshold.

15. An electro-therapeutic device for treating the preferably human body, and/or for carrying out a respirator-triggered, active expiration and/or for the prophylaxis of an inactivity atrophy of the respiratory muscle disorder, with electrical currents of a defined frequency and amplitude, comprising at least two flat electrodes attachable to the body to be treated for closing a current circuit via said body, in connection with which device a treatment current ($i_B$) whose amplitude (A) and frequency (f) can be modulated simultaneously, can be introduced into the body to be treated, means for varying the treatment current ($i_B$) within a frequency band ($f_B$) designated as the medium frequency range between from 1kHz to 100kHz, in order to treat the preferably human body, or to carry out said active expiration or to treat said respiratory disorder, in a manner such that it is varied in preferably discrete frequency steps between a first limit value with a low limit frequency ($f_u$) at a simultaneously minimal amplitude ($A_u$) of the treatment current ($i_B$), and a second limit value with an upper limit frequency ($f_o$) with a maximal amplitude ($A_o$) of the treatment current ($i_B$) and a second limit value with an upper limit frequency ($f_o$) with a minimal amplitude ($A_u$) of the treatment current ($i_B$), means for causing amplitude rises or drops as the frequency is simultaneously increasing, or, vice-versa, the amplitude (A) of the treatment current ($i_B$) decreases or rises as the frequency is simultaneously decreasing, and means for modulating the treatment current ($i_B$) in such a manner that it is varied at least within a part of the treatment frequency band ($f_B$) between the first and the second limit values in a manner such that it is varied slightly below the threshold based on a stimulation threshold (RS), substantially in parallel with the stimulation threshold (RS), in a manner such that the treatment current ($i_b$) is always trailing the stimulation threshold (RS) depending upon the amplitude and the frequency, in each case slightly falling short of the sensitivity threshold; and wherein treatment is run from a specific lower limit through to a specific upper limit, before the procedure is restarted on another level.

* * * * *